(12) United States Patent
Gephart et al.

(10) Patent No.: US 8,657,856 B2
(45) Date of Patent: Feb. 25, 2014

(54) SIZE TRANSITION SPINAL ROD

(75) Inventors: Matthew P. Gephart, Marquette, MI (US); Thomas S. Kilpela, Marquette, MI (US); John Sullivan, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 12/871,893

(22) Filed: Aug. 30, 2010

(65) Prior Publication Data

US 2011/0054535 A1    Mar. 3, 2011

Related U.S. Application Data

(60) Provisional application No. 61/237,896, filed on Aug. 28, 2009.

(51) Int. Cl.
    *A61B 17/70* (2006.01)

(52) U.S. Cl.
    USPC .................... 606/254; 606/256; 606/257

(58) Field of Classification Search
    USPC .................................... 606/246–279
    See application file for complete search history.

(56) References Cited

U.S. PATENT DOCUMENTS

| | | | |
|---|---|---|---|
| 4,041,939 A | 8/1977 | Hall | |
| 4,369,769 A | 1/1983 | Edwards | |
| 4,648,388 A * | 3/1987 | Steffee | 606/261 |
| 4,697,582 A | 10/1987 | William | |
| 4,743,260 A | 5/1988 | Burton | |
| 4,773,402 A | 9/1988 | Asher et al. | |
| 4,815,453 A | 3/1989 | Cotrel | |
| 4,920,959 A | 5/1990 | Witzel et al. | |
| 5,000,165 A | 3/1991 | Watanabe | |
| 5,005,562 A | 4/1991 | Cotrel | |
| 5,024,213 A * | 6/1991 | Asher et al. | 606/278 |
| 5,030,220 A | 7/1991 | Howland | |
| 5,129,899 A | 7/1992 | Small et al. | |
| 5,133,717 A | 7/1992 | Chopin | |
| 5,147,360 A | 9/1992 | Dubousset | |
| 5,217,461 A * | 6/1993 | Asher et al. | 606/261 |
| 5,242,443 A * | 9/1993 | Kambin | 606/60 |
| 5,282,863 A | 2/1994 | Burton | |
| 5,290,289 A | 3/1994 | Sanders et al. | |
| 5,415,661 A | 5/1995 | Holmes | |
| 5,437,669 A | 8/1995 | Yuan et al. | |
| 5,486,174 A * | 1/1996 | Fournet-Fayard et al. | 606/261 |
| 5,488,761 A | 2/1996 | Leone | |
| 5,536,268 A | 7/1996 | Griss | |
| 5,575,790 A | 11/1996 | Chen et al. | |
| 5,586,983 A | 12/1996 | Sanders et al. | |
| 5,593,408 A | 1/1997 | Gayet et al. | |

(Continued)

FOREIGN PATENT DOCUMENTS

| | | |
|---|---|---|
| CN | 200998298 Y | 8/2006 |
| DE | 202008002415 U1 | 7/2008 |

(Continued)

*Primary Examiner* — Jan Christopher Merene
(74) *Attorney, Agent, or Firm* — Fitch, Even, Tabin & Flannery LLP

(57) ABSTRACT

Spinal rods are provided that transition from one diameter to another without an extended transition region to which coupling devices may not be attached, allowing coupling devices for mounting the spinal rod to the spine to be secured almost anywhere along the rod's length without having a weakened transition point.

3 Claims, 14 Drawing Sheets

(56) References Cited

U.S. PATENT DOCUMENTS

| | | |
|---|---|---|
| 5,658,286 A | 8/1997 | Sava |
| 5,667,507 A | 9/1997 | Corin et al. |
| 5,672,175 A | 9/1997 | Martin |
| 5,702,395 A | 12/1997 | Hopf |
| 5,704,936 A | 1/1998 | Mazel |
| 5,769,851 A | 6/1998 | Veith |
| 5,800,434 A | 9/1998 | Campbell et al. |
| 5,947,965 A | 9/1999 | Bryan |
| 5,976,133 A | 11/1999 | Kraus et al. |
| 6,015,409 A | 1/2000 | Jackson |
| 6,099,528 A | 8/2000 | Saurat |
| 6,102,912 A | 8/2000 | Cazin et al. |
| 6,139,548 A | 10/2000 | Errico |
| 6,159,211 A | 12/2000 | Boriani |
| 6,210,413 B1 | 4/2001 | Justis et al. |
| 6,283,965 B1 | 9/2001 | Ballier |
| 6,287,308 B1 | 9/2001 | Betz et al. |
| 6,293,949 B1 | 9/2001 | Justis et al. |
| 6,296,644 B1 | 10/2001 | Saurat et al. |
| RE37,479 E | 12/2001 | Kuslich |
| 6,325,802 B1 | 12/2001 | Frigg |
| 6,325,805 B1 | 12/2001 | Ogilvie |
| 6,340,361 B1 | 1/2002 | Kraus et al. |
| 6,488,682 B2 | 12/2002 | Kikuchi et al. |
| 6,554,831 B1 | 4/2003 | Rivard et al. |
| 6,558,386 B1 | 5/2003 | Cragg |
| 6,558,390 B2 | 5/2003 | Cragg |
| 6,572,619 B2 | 6/2003 | Santilli |
| 6,592,585 B2 | 7/2003 | Lee et al. |
| 6,610,061 B2 | 8/2003 | Ballier |
| 6,613,051 B1 | 9/2003 | Luk et al. |
| 6,706,044 B2 | 3/2004 | Kuslich et al. |
| 6,749,614 B2 | 6/2004 | Teitelbaum et al. |
| 6,761,719 B2 | 7/2004 | Justis et al. |
| 6,802,844 B2 | 10/2004 | Ferree |
| 6,875,212 B2 | 4/2005 | Shaolian et al. |
| 6,899,713 B2 | 5/2005 | Shaolian et al. |
| 6,899,716 B2 | 5/2005 | Cragg |
| 6,921,403 B2 | 7/2005 | Cragg et al. |
| 6,964,667 B2 | 11/2005 | Shaolian |
| 6,986,771 B2 | 1/2006 | Paul et al. |
| RE39,035 E | 3/2006 | Finn et al. |
| 7,083,621 B2 | 8/2006 | Shaolian |
| 7,125,410 B2 | 10/2006 | Freudiger |
| 7,220,262 B1 | 5/2007 | Hynes |
| 7,309,338 B2 | 12/2007 | Cragg |
| 7,326,210 B2 | 2/2008 | Jahng et al. |
| 7,329,259 B2 | 2/2008 | Cragg |
| 7,377,921 B2 | 5/2008 | Studer et al. |
| 7,594,924 B2 * | 9/2009 | Albert et al. ............... 606/267 |
| 7,763,052 B2 * | 7/2010 | Jahng ........................ 606/254 |
| 7,806,913 B2 * | 10/2010 | Fanger et al. ............. 606/260 |
| 2002/0052603 A1 | 5/2002 | Nichols et al. |
| 2002/0087159 A1 | 7/2002 | Thomas |
| 2002/0120269 A1 | 8/2002 | Lange |
| 2003/0060824 A1 | 3/2003 | Viart |
| 2003/0100897 A1 | 5/2003 | Metz-Stavenhagen |
| 2003/0171751 A1 | 9/2003 | Ritland |
| 2003/0225408 A1 | 12/2003 | Nichols et al. |
| 2004/0033295 A1 | 2/2004 | Gimelli et al. |
| 2004/0143264 A1 | 7/2004 | McAfee |
| 2004/0210226 A1 | 10/2004 | Trieu |
| 2004/0215191 A1 | 10/2004 | Kitchen |
| 2004/0215192 A1 | 10/2004 | Justis et al. |
| 2004/0215193 A1 | 10/2004 | Shaolian et al. |
| 2005/0033295 A1 | 2/2005 | Wisnewski |
| 2005/0065516 A1 | 3/2005 | Jahng |
| 2005/0085810 A1 | 4/2005 | Lutz et al. |
| 2005/0085812 A1 | 4/2005 | Sherman et al. |
| 2005/0085814 A1 | 4/2005 | Sherman et al. |
| 2005/0085815 A1 | 4/2005 | Harms et al. |
| 2005/0101953 A1 | 5/2005 | Simonson |
| 2005/0113831 A1 | 5/2005 | Franck |
| 2005/0131407 A1 | 6/2005 | Sicvol et al. |
| 2005/0137594 A1 | 6/2005 | Doubler et al. |
| 2005/0143823 A1 | 6/2005 | Boyd et al. |
| 2005/0149020 A1 | 7/2005 | Jahng |
| 2005/0154390 A1 * | 7/2005 | Biedermann et al. ........... 606/61 |
| 2005/0154466 A1 | 7/2005 | Humphreys et al. |
| 2005/0177157 A1 | 8/2005 | Jahng |
| 2005/0187548 A1 | 8/2005 | Butler et al. |
| 2005/0203513 A1 | 9/2005 | Jahng et al. |
| 2005/0203514 A1 | 9/2005 | Jahng et al. |
| 2005/0203518 A1 | 9/2005 | Biedermann et al. |
| 2005/0203519 A1 | 9/2005 | Harms et al. |
| 2005/0209694 A1 | 9/2005 | Loeb |
| 2005/0277919 A1 | 12/2005 | Slivka et al. |
| 2005/0277934 A1 | 12/2005 | Vardiman |
| 2005/0283159 A1 | 12/2005 | Amara |
| 2006/0025767 A1 | 2/2006 | Khalili |
| 2006/0041259 A1 | 2/2006 | Paul et al. |
| 2006/0052786 A1 | 3/2006 | Dant et al. |
| 2006/0064090 A1 | 3/2006 | Park |
| 2006/0074418 A1 | 4/2006 | Jackson |
| 2006/0074445 A1 | 4/2006 | Gerber et al. |
| 2006/0084980 A1 | 4/2006 | Melkent et al. |
| 2006/0084989 A1 | 4/2006 | Dickinson |
| 2006/0142758 A1 | 6/2006 | Petit |
| 2006/0184171 A1 | 8/2006 | Biedermann et al. |
| 2006/0190081 A1 | 8/2006 | Kraus |
| 2006/0195093 A1 | 8/2006 | Jahng |
| 2006/0195094 A1 | 8/2006 | McGraw et al. |
| 2006/0195096 A1 | 8/2006 | Lee |
| 2006/0200128 A1 | 9/2006 | Mueller |
| 2006/0212033 A1 | 9/2006 | Rothman et al. |
| 2006/0229607 A1 | 10/2006 | Brumfield |
| 2006/0229608 A1 | 10/2006 | Foster et al. |
| 2006/0229615 A1 | 10/2006 | Abdou |
| 2006/0235390 A1 | 10/2006 | Zhang et al. |
| 2006/0241595 A1 | 10/2006 | Molz, IV et al. |
| 2006/0247630 A1 | 11/2006 | Lott |
| 2006/0247638 A1 | 11/2006 | Trieu et al. |
| 2006/0260483 A1 * | 11/2006 | Hartmann et al. ............. 101/216 |
| 2006/0264934 A1 | 11/2006 | Fallin |
| 2006/0265074 A1 | 11/2006 | Krishna |
| 2006/0271051 A1 | 11/2006 | Berrevoets et al. |
| 2007/0016190 A1 | 1/2007 | Martinez et al. |
| 2007/0016200 A1 * | 1/2007 | Jackson ........................ 606/61 |
| 2007/0038217 A1 | 2/2007 | Brown et al. |
| 2007/0049936 A1 | 3/2007 | Colleran |
| 2007/0049937 A1 * | 3/2007 | Matthis et al. .................. 606/61 |
| 2007/0055235 A1 | 3/2007 | Janowski et al. |
| 2007/0055242 A1 | 3/2007 | Bailly |
| 2007/0078460 A1 | 4/2007 | Frigg |
| 2007/0083201 A1 | 4/2007 | Jones |
| 2007/0083210 A1 | 4/2007 | Hestad et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0100341 A1 | 5/2007 | Reglos et al. |
| 2007/0118120 A1 | 5/2007 | Stevenson |
| 2007/0118122 A1 | 5/2007 | Butler et al. |
| 2007/0123865 A1 | 5/2007 | Schlapfer et al. |
| 2007/0123871 A1 | 5/2007 | Jahng |
| 2007/0129729 A1 | 6/2007 | Petit et al. |
| 2007/0156145 A1 | 7/2007 | Demakas et al. |
| 2007/0161987 A1 | 7/2007 | Capote |
| 2007/0161993 A1 | 7/2007 | Lowery et al. |
| 2007/0161999 A1 | 7/2007 | Biedermann et al. |
| 2007/0162007 A1 | 7/2007 | Shoham |
| 2007/0162010 A1 | 7/2007 | Chao et al. |
| 2007/0167948 A1 | 7/2007 | Abdou |
| 2007/0167954 A1 | 7/2007 | Sicvol |
| 2007/0168039 A1 | 7/2007 | Trieu |
| 2007/0173800 A1 | 7/2007 | Sanders et al. |
| 2007/0173819 A1 | 7/2007 | Sandlin |
| 2007/0173820 A1 | 7/2007 | Trieu |
| 2007/0173821 A1 | 7/2007 | Trieu |
| 2007/0173828 A1 | 7/2007 | Firkins et al. |
| 2007/0173833 A1 | 7/2007 | Butler et al. |
| 2007/0179501 A1 | 8/2007 | Firkins |
| 2007/0191831 A1 | 8/2007 | Sanders et al. |

(56) References Cited

U.S. PATENT DOCUMENTS

| | | |
|---|---|---|
| 2007/0191841 A1 | 8/2007 | Justis et al. |
| 2007/0191845 A1 | 8/2007 | Justis et al. |
| 2007/0191846 A1 | 8/2007 | Bruneau et al. |
| 2007/0213717 A1 | 9/2007 | Trieu et al. |
| 2007/0213718 A1 | 9/2007 | Trieu |
| 2007/0225710 A1 | 9/2007 | Jahng et al. |
| 2007/0233064 A1 | 10/2007 | Holt |
| 2007/0233085 A1 | 10/2007 | Biedermann et al. |
| 2007/0233095 A1 | 10/2007 | Schlaepfer |
| 2007/0233099 A1 | 10/2007 | Cragg |
| 2007/0233260 A1 | 10/2007 | Cragg |
| 2007/0270802 A1 | 11/2007 | Kodkani |
| 2007/0276380 A1 | 11/2007 | Jahng et al. |
| 2007/0288008 A1 | 12/2007 | Park |
| 2007/0288013 A1 | 12/2007 | Sanders |
| 2007/0293862 A1 | 12/2007 | Jackson |
| 2008/0021461 A1 | 1/2008 | Barker et al. |
| 2008/0021465 A1 | 1/2008 | Shadduck et al. |
| 2008/0021469 A1 | 1/2008 | Holt |
| 2008/0021474 A1 | 1/2008 | Bonutti et al. |
| 2008/0033432 A1 | 2/2008 | McGraw et al. |
| 2008/0039845 A1 | 2/2008 | Bonutti et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058812 A1* | 3/2008 | Zehnder .................... 606/61 |
| 2008/0065071 A1 | 3/2008 | Park |
| 2008/0071273 A1 | 3/2008 | Hawkes et al. |
| 2008/0086127 A1 | 4/2008 | Patterson et al. |
| 2008/0097431 A1 | 4/2008 | Vessa |
| 2008/0125777 A1 | 5/2008 | Veldman et al. |
| 2008/0147120 A1 | 6/2008 | Molz et al. |
| 2008/0161853 A1 | 7/2008 | Arnold et al. |
| 2008/0161863 A1 | 7/2008 | Arnold et al. |
| 2008/0172091 A1 | 7/2008 | Anderson |
| 2008/0177316 A1 | 7/2008 | Bergeron et al. |
| 2008/0177317 A1 | 7/2008 | Jackson |
| 2008/0177320 A1 | 7/2008 | McBride |
| 2008/0177326 A1 | 7/2008 | Thompson |
| 2008/0183212 A1 | 7/2008 | Veldman et al. |
| 2008/0183213 A1 | 7/2008 | Veldman et al. |
| 2008/0183216 A1 | 7/2008 | Jackson |
| 2008/0188898 A1 | 8/2008 | Jackson |
| 2008/0195153 A1 | 8/2008 | Thompson |
| 2008/0195159 A1 | 8/2008 | Kloss et al. |
| 2008/0200952 A1 | 8/2008 | Moorcroft et al. |
| 2008/0208256 A1 | 8/2008 | Thramann |
| 2008/0221620 A1 | 9/2008 | Krause |
| 2008/0234738 A1 | 9/2008 | Zylber et al. |
| 2008/0234744 A1 | 9/2008 | Zylber et al. |
| 2008/0234746 A1 | 9/2008 | Jahng et al. |
| 2009/0099606 A1* | 4/2009 | Hestad et al. .................. 606/254 |
| 2010/0114165 A1* | 5/2010 | Ely ............................... 606/246 |

FOREIGN PATENT DOCUMENTS

| | | |
|---|---|---|
| EP | 470660 A1 | 7/1991 |
| EP | 683744 B1 | 6/2000 |
| EP | 1364622 B1 | 3/2003 |
| EP | 1454593 A1 | 9/2004 |
| EP | 1322241 B1 | 7/2006 |
| EP | 1792577 A1 | 7/2007 |
| EP | 1810624 A1 | 7/2007 |
| KR | 2006119653 A | 11/2006 |
| WO | 9913265 A1 | 11/1990 |
| WO | 9615729 A1 | 5/1996 |
| WO | 9732533 A1 | 9/1997 |
| WO | 2005092222 A1 | 10/2005 |
| WO | 2006066053 A1 | 6/2006 |
| WO | 2006101737 A1 | 9/2006 |
| WO | 2007103404 A2 | 9/2007 |

* cited by examiner

SIZE TRANSITION SPINAL ROD

FIELD OF THE INVENTION

The inventions provided herein relate to generally rigid elongate members for connecting and partially or fully immobilizing two or more vertebrae of the spine. More specifically, the inventions relate to elongate members for immobilizing two or more vertebrae from different regions of the spine, such as the cervical and thoracic regions.

BACKGROUND

The human spinal column includes a number of vertebrae of different sizes. The cervical vertebrae, forming the neck area, are relatively small. Just below the cervical vertebrae are the thoracic vertebrae, which form the upper back. The thoracic vertebrae are larger than the cervical vertebrae, and increase in size from top to bottom. Below the thoracic region lie the lumbar vertebrae, which are still larger. Injuries to different parts of the spine may necessitate different types of treatment, based on the type and extent of the injury as well as the size and density of bone at the site of the injury. For instance, certain spinal injuries or deformities require fixation or immobilization of adjacent vertebrae, with rigid members of appropriate stiffness anchored to the vertebrae in order to brace them and limit movement.

Various devices for internal fixation of bone segments in the human or animal body are known in the art. For instance, pedicle screw and/or hook systems are sometimes used as an adjunct to spinal fusion surgery, and provide a means of securing spinal rods or other elongate members to two or more vertebrae. Such systems may have a rod-receiving portion and an integral anchor portion, or may be provided with a separate anchor member, especially one that may be pivoted with respect to a rod-receiving member. The rod-receiving portions of the devices (also referred to as coupling devices) couple to the pedicle screw or hook and receive an elongate members such as a spinal rod (commonly referred to as a distraction rod). Two or more rod receiving devices are inserted into respective vertebrae and adjusted along the spinal rod to distract, de-rotate, and/or stabilize a spinal column, for instance to correct scoliosis or stabilize the spinal column in conjunction with an operation to correct a herniated disk. One goal of such a system is to substantially reduce and/or prevent relative motion between the spinal segments that are being fused.

The size, positioning, and curvature of the cervical spine present surgeons with different challenges than the lumbar spine. For instance, since the cervical vertebrae are relatively small and spaced closely together, the devices used to anchor a spinal rod to the bone must be small enough to be placed in close proximity without abutting one another. Furthermore, anchoring a spinal rod to cervical vertebrae with large screws or other anchor devices designed for lumbar use may destroy or irreparably damage the small cervical vertebrae. Therefore, smaller anchor members are usually utilized in the cervical region. In addition, the gauge or stiffness of the spinal rods used in the cervical region ordinarily differs from that used in the thoracic or lumbar regions, since a larger and less flexible spinal rod may provide enough force to pull anchor members out of cervical vertebral bone.

In many cases where an immobilization system must span the cervical and thoracic vertebrae, and potentially the lumbar vertebrae as well, the ability to connect a smaller diameter cervical spinal rod with a larger diameter thoracic/lumbar spinal rod must be provided. Specialized spinal rods that transition from a narrower portion for cervical use to a wider portion for thoracic/lumbar use have been designed. However, those rods usually have a long tapered portion to transition from one region to another. Since this tapered transition portion has a constantly changing diameter, coupling devices may not be secured to the rod along the transition portion, creating a large amount of unusable space along the length of the spinal rod. Since spinal rods are usually made of relatively inflexible materials, such as titanium or stainless steel, without a long transition portion the abrupt transition between the narrower, more flexible cervical portion and the wider, stiffer thoracic/lumbar portion will create significant stress at the transition juncture, which could cause sheering of the rod at that point.

SUMMARY

Novel spinal rods are provided herein that transition from one diameter to another without the aforementioned problems, allowing coupling devices to be secured almost anywhere along the rod's length and without having a weakened transition point. In one form, a series of cuts or grooves may be provided along the spinal rod to provide a region of gradually decreasing flexibility while maintaining a relatively constant overall profile. In another form, a narrower rod portion is coupled to a wider rod portion through a flexible joint that reduces localized stress at the point of transition between the rod portions, allowing for a relatively short transition region. The transition region is more flexible than the larger or more rigid rod portion. In another form, the spinal rod may be formed of a material such as cobalt-chromium or similar alloys in order to provide a more resilient rod that resists wear and consequently may have a shorter transition region.

DETAILED DESCRIPTION

Spinal rods provided herein are generally cylindrical and have at least two portions, a wide portion having a larger diameter for coupling to larger vertebrae and a narrow portion having a smaller diameter for coupling to smaller vertebrae. The at least two portions are coupled together in a flexible manner so as to avoid concentration of stresses at a single point or small area of transition between the wider portion and narrow portion, which could result in failure or shearing of the rod at the transition area between the two portions.

Figure 1:
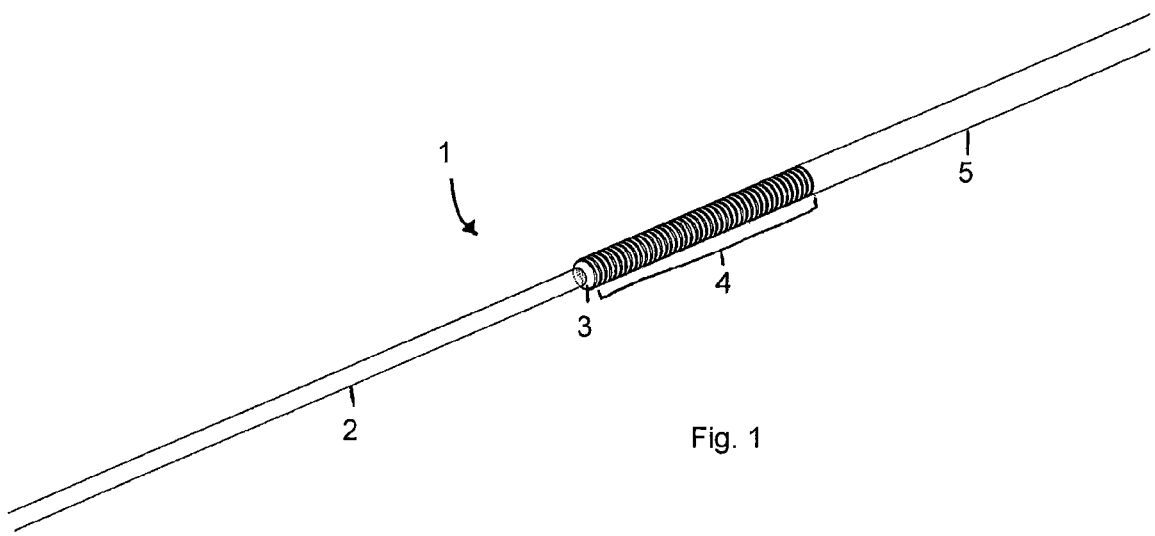
FIG. 1 is a perspective view of one spinal rod for connecting two or more vertebrae of different sizes.

One embodiment of such a spinal rod is shown in FIG. 1. The exemplary spinal rod 1 of FIG. 1 includes a cervical region 2, a short tapered region 3, a region of variable flexibility 4, and a solid thoracic/lumbar region 5. The diameter of the cervical region 2 may be, for instance, about 3.2 mm while the larger diameter of the thoracic/lumbar region may be, for instance about 5.5 mm. Of course, different diameters of rods are also contemplated, as long as one portion of the rod has a diameter that differs from that of another portion of the rod.

Figure 2:
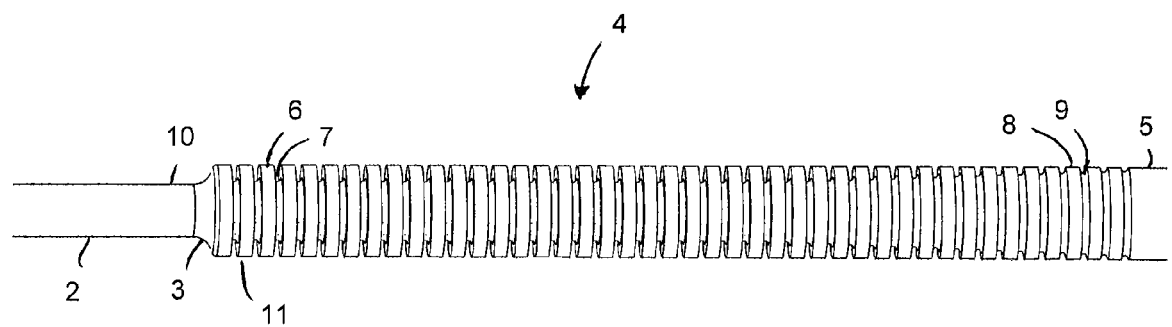
FIG. 2 is a magnified view of the transition region of the spinal rod of FIG. 1.

As seen in FIG. 2, the rod may include a very short tapered portion 3 transitioning from a first diameter to a second diameter. The rod then includes a region of variable flexibility 4 that includes a series of cuts or grooves of varying depth. In the embodiment shown in FIG. 2, the grooves are discontinuous, annular grooves that are relatively narrow and spaced from one another. The depth of the grooves decreases toward the wider rod portion 5 Thus, while the region 4 has an overall profile that matches the wider portion of the rod 5, its flexibility at one end is closer to that of the narrower rod portion 2 and closer to the flexibility of the wider portion 5 at the other end.

Figure 3:
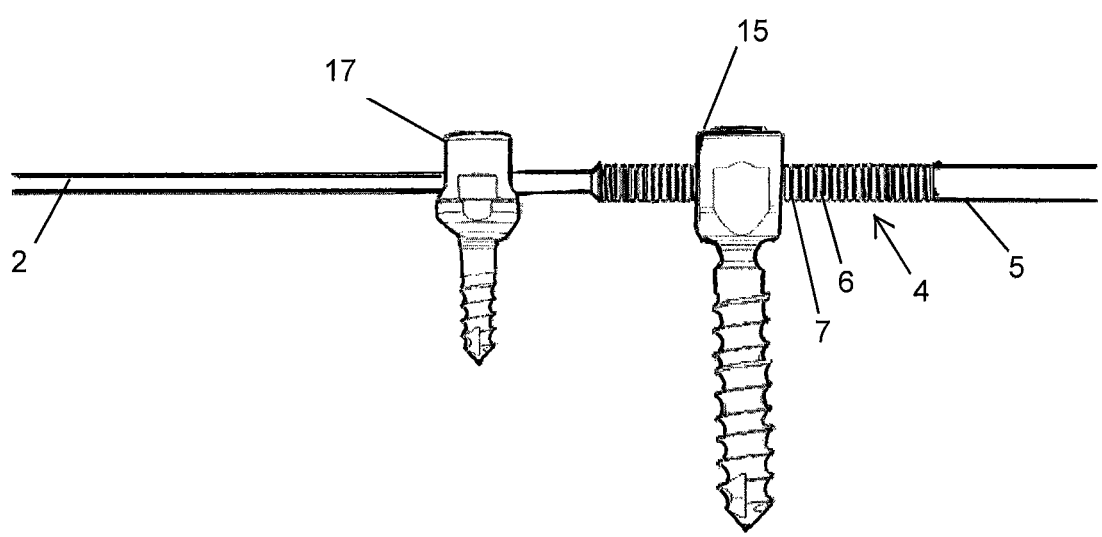
FIG. 3 shows the spinal rod from FIG. 1 coupled to two pedicle screws of different sizes, one designed for anchoring to a cervical vertebra and one for anchoring to a thoracic or lumbar vertebra.

The depth of the grooves in the variable flexibility region 4 gradually decreases from the thoracic/lumbar region 5 to the cervical region 2, so that annular grooves close to the wider rod portion 5, such as groove 9, are much shallower than grooves located closer to the narrower rod portion 2, such as groove 7, providing almost constantly decreasing flexibility from its beginning toward the end adjacent the wider rod portion 5. However, portions of the rod adjacent these grooves, such as regions 6 and 8, are of the same diameter. Thus, instead of being frusto-conical and tapering from the wider diameter of the thoracic/lumbar region 5 to the narrower diameter of the cervical region 2, the transition region 4 has a cylindrical overall outer profile similar to that of the wider thoracic/lumbar portion, giving the transition portion a constant effective diameter that can be matched to an appropriate coupling device. Therefore, a coupling device for securing the rod to the vertebrae, such as a pedicle screw or hook, may be matched to the effective diameter and attached to the rod at any point along the variable flexibility region 4. This allows, for instance, a cervical pedicle screw assembly to be attached at a point 10 directly adjacent to the transition region 3 and a thoracic pedicle screw assembly to be attached at a point 11 just on the other side of the transition region 3. Cervical and thoracic pedicle screw assemblies are shown mounted to the rod in FIG. 3.

The variable flexibility region 4 effectively distributes stress resulting from the rod's diameter change from one region to another along a significant length of the rod, reducing stress risers that would otherwise result at the abrupt transition region 3. Two or more variable flexibility regions may also be provided if necessary or desired. Preferably, the rod 1 comprises cobalt-chromium or similar alloys in order to better handle stresses exerted upon the rod by the spine.

Figure 4:
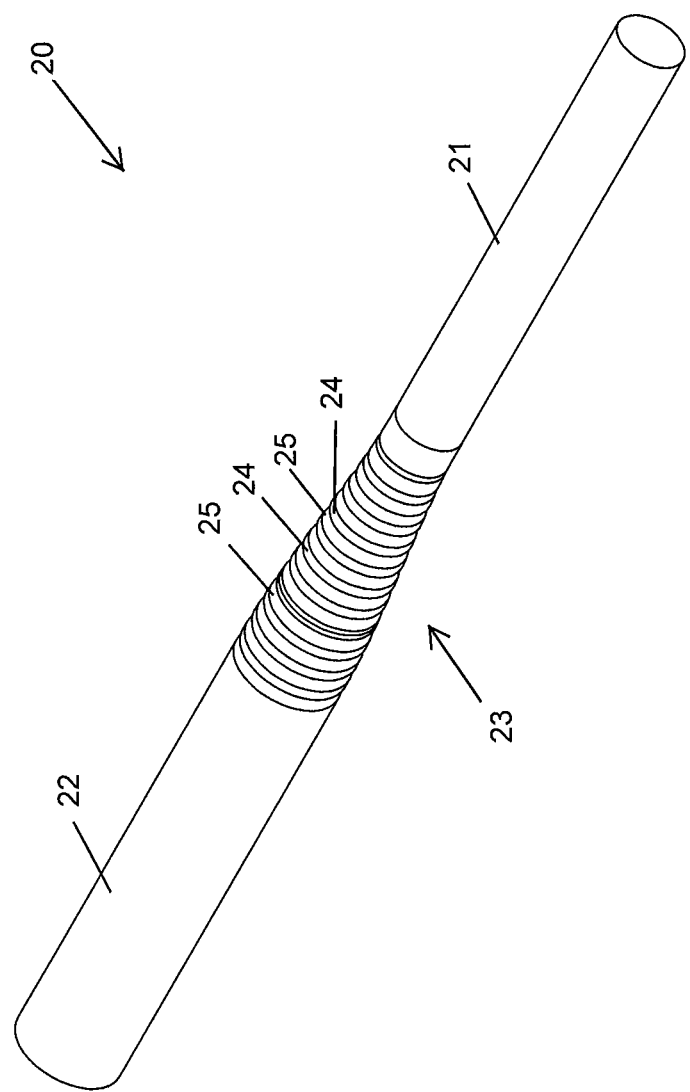
FIG. 4 is a perspective view of a spinal rod with a tapered transition region including a number of annular grooves.
Figure 5:
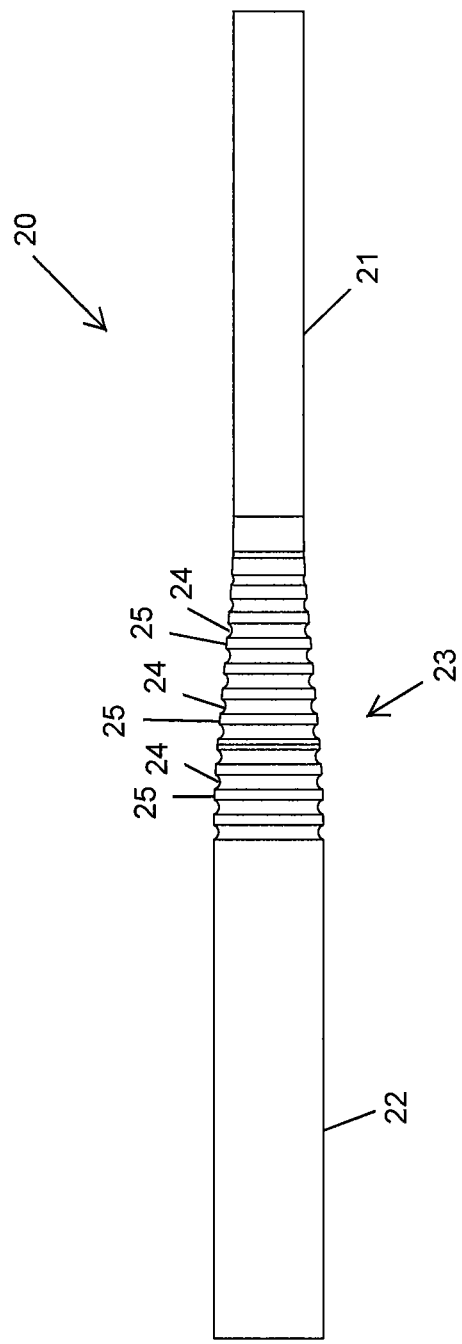
FIG. 5 is a side view of the spinal rod from FIG. 4.

FIGS. 4 and 5 illustrate another form of spinal rod 20 having a transition between a narrower diameter portion 21 and a wider diameter portion 22. A tapered transition region 23 includes a series of coaxial annular grooves 24 disposed thereon, forming raised annular ridges 25 therebetween. As illustrated, the grooves 24 are disposed at relatively regular intervals along the transition region 23, but the spacing and depth of the grooves may be varied as desired in order to provide a desired amount of flexibility in order to distribute stresses imparted to the non-grooved rod portions 21 and 22 over a relatively large area. The length of the transition region 23 and the depth and spacing of the grooves 24 may vary as needed to provide an adequately gradual transition in elasticity from the cervical rod region 21 to the thoracic/lumbar region 22. The non-helical grooves 24 allow the flexibility of the transition region 23 to be altered in a relatively short space. The spinal rod 20 may be made of any suitable material, such as stainless steel, titanium, cobalt-chromium alloys, nickel-titanium alloys, or polyetheretherketone (PEEK) or other similar polymers, such as polymer of the poly-arylether-ketone family such as, but not limited to, poly-etherketone (PEK) and poly-ether-ketone-ether-ketone-ketone (PEKEKK). The type of spinal rod 20 depicted in FIGS. 4 and 5 is preferably a unitary construct, avoiding fastening the two rod regions 21 and 22 with features such as threaded surfaces that increase stress when forces are applied to one or both of the rod regions.

Figure 6:
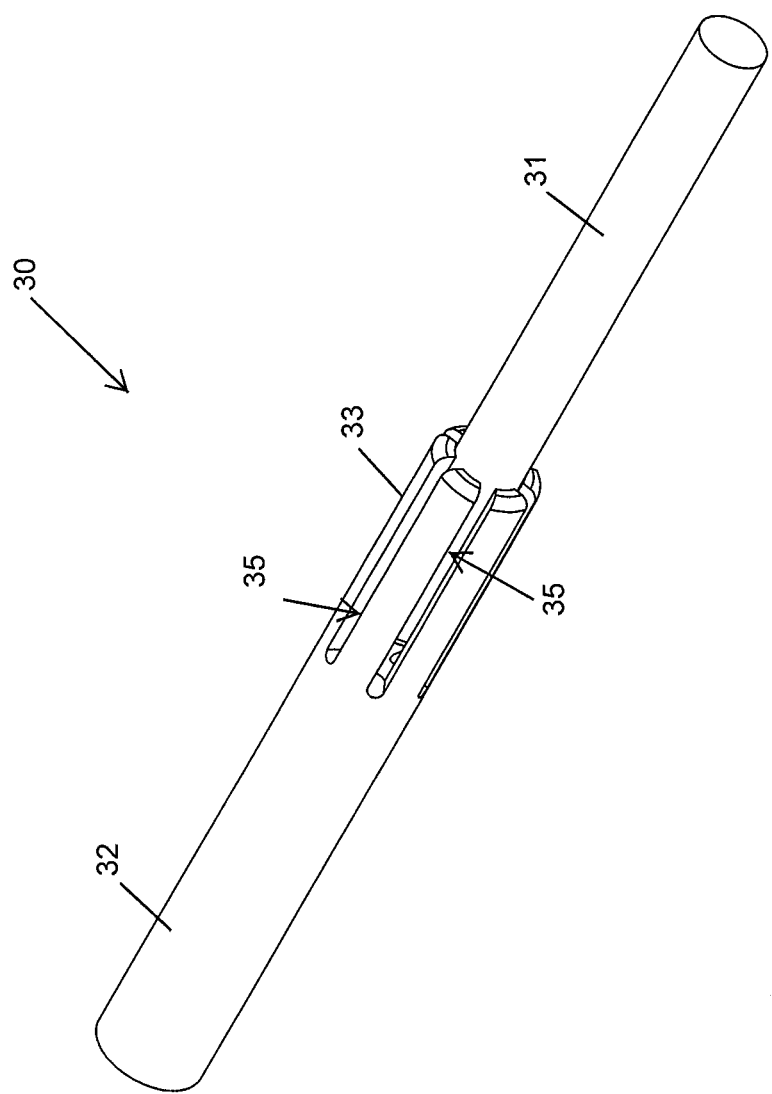
FIG. 6 is a perspective view of a spinal rod wherein a first rod portion is received within a bore at the end of a second rod portion.
Figure 7:
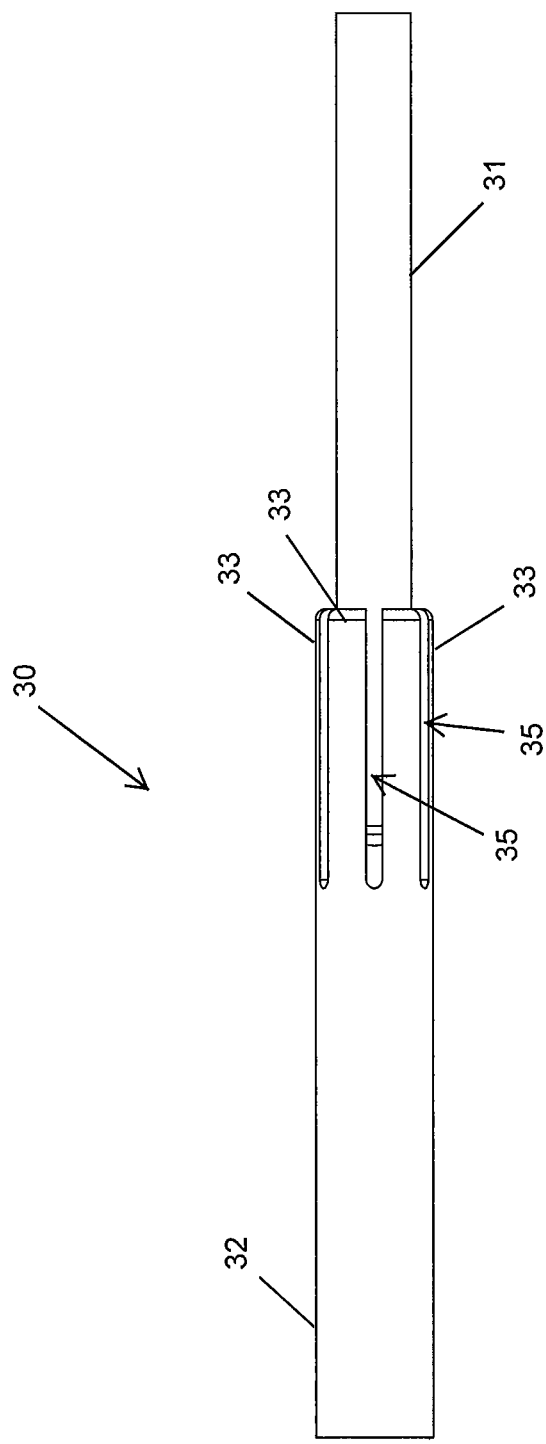
FIG. 7 is a side view of the spinal rod from FIG. 6
Figure 8:
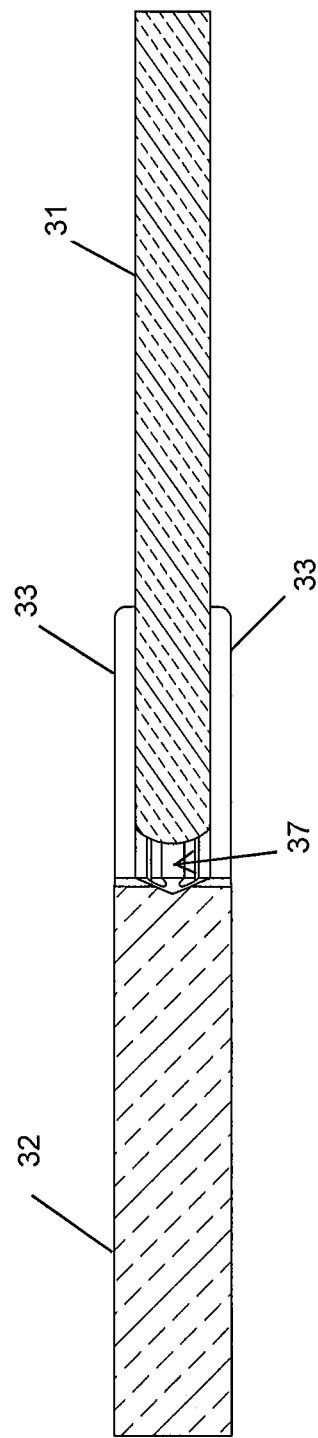
FIG. 8 is a cross-sectional view of the spinal rod from FIG. 6.

FIGS. 6-8 illustrate a spinal rod 30 wherein two separate rod portions 31 and 32 having different diameters are coupled together to form a continuous rod. The larger diameter rod portion, such as thoracic/lumbar rod portion 32, includes an axial bore 37 configured to receive one end of the narrower diameter rod portion, such as cervical rod portion 31. The end of the thoracic/lumbar rod portion 32 that holds the cervical rod portion 31 includes a plurality of slits 35 that separate the end of the larger rod portion 32 into a plurality of finger-like projections 33. The projections allow some flexibility between the thoracic/lumbar rod portion 32 and the cervical rod portion 31. As seen in FIG. 8, a small space may be provided at the end of the bore 37 when the cervical rod portion 31 is disposed therein, allowing some slight axial micromotion translation between the rod portions if desired. Alternatively, the cervical rod portion 31 may be fitted tightly within the bore 37. If desired, a polymer sleeve may be inserted between the projections 33.

The length and width of the projections 33 and the width and number of slits 35 therebetween may be varied as desired in order to provide the desired amount of flexibility between the thoracic/lumbar rod portion 32 and the cervical rod portion 31. The rod portions may be made up of stainless steel, titanium, cobalt chromium, nickel-titanium alloys, PEEK or similar polymers, or other suitable materials.

Figure 9:
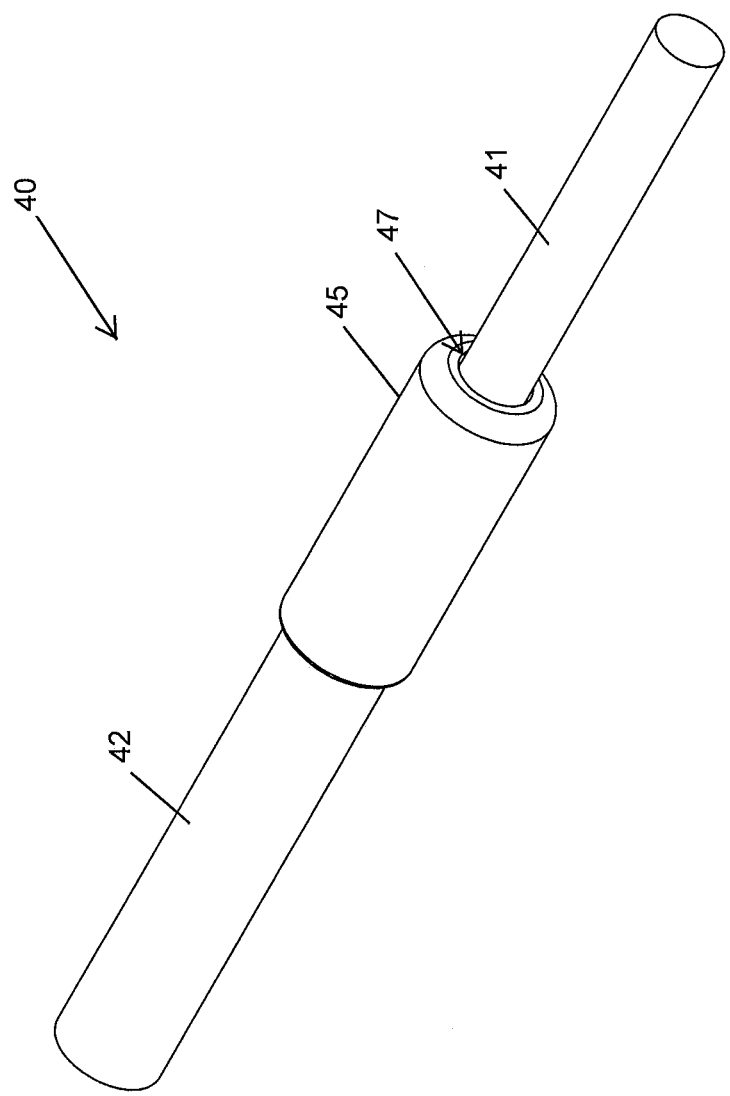
FIG. 9 is a perspective view of a spinal rod wherein a first rod portion is received within a cap portion at the end of a second rod portion.
Figure 10:
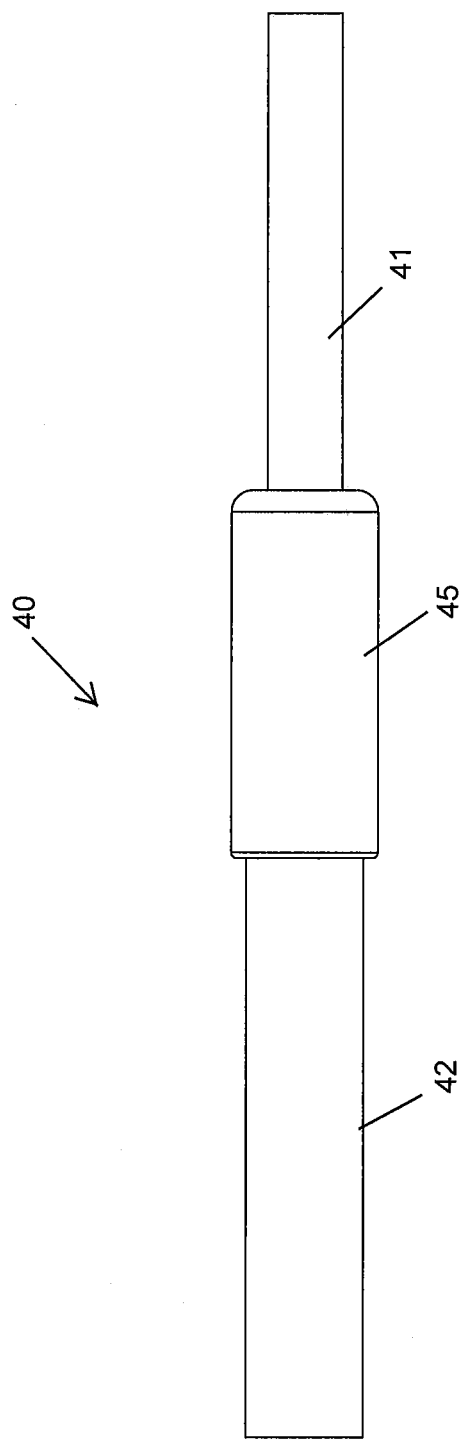
FIG. 10 is a side view of the spinal rod from FIG. 9.
Figure 11:
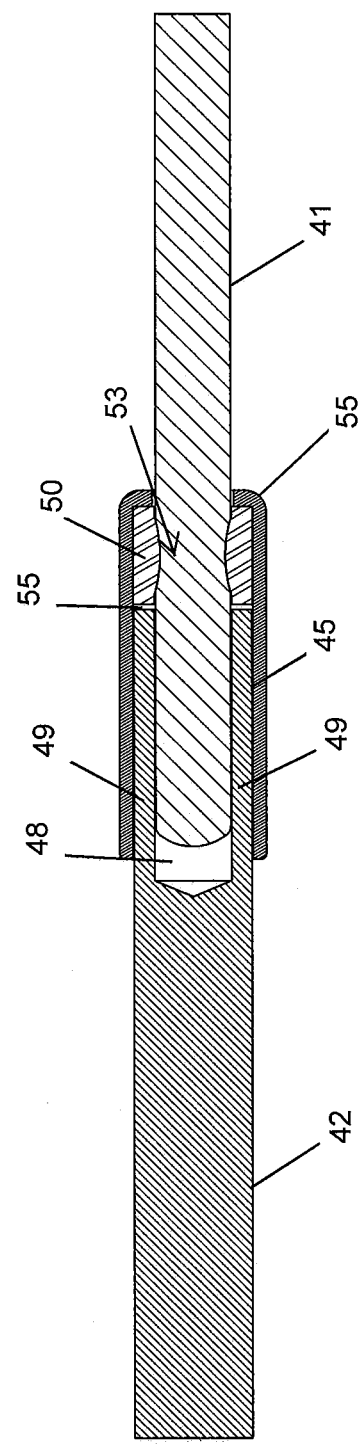
FIG. 11 is a cross-sectional view of the spinal rod from FIG. 9.

Another spinal rod 40 having a short transition region between a smaller diameter rod portion, such as cervical rod portion 41, and a larger diameter rod portion, such as thoracic/lumbar rod portion 42, is shown in FIGS. 9-11. The device shown has a cap portion 45 covering the transition region, one end of the cap portion 45 including an opening 47 for receiving the cervical rod portion 41. The cross-sectional view in FIG. 11 shows that the cervical rod portion 41 is received within a bore 48 at one end of the thoracic/lumbar rod portion 42. The side surfaces 49 of the thoracic/lumbar rod portion 42 surrounding the bore 48 hold the cervical rod portion 41 in place, and the fit between the two rod portions may be adjusted depending on the desired flexibility of the transition region. The two rod portions are preferably coupled without structures such as threads that can cause unwanted stress between the rod portions when one or both rod portions are bent or twisted.

The cap portion 45 shown in FIG. 11 may be a separate member coupled to the thoracic/lumbar rod portion 42, or may be formed as a unitary portion of the rod 42. Preferably, if the cap portion 45 is a separate component, it is coupled to the rod 42 without threads or similar physical connection structures. A separate bumper member 50 may be included in order to limit translation of the cervical rod portion 41 relative to the thoracic/lumbar rod portion 42 and to absorb some of the force placed on the rods. Preferably the bumper portion 50 is made of PEEK or another polymer of the poly-aryl-ether-ketone family, or other polymers. The cervical rod portion 41 may include a narrowed portion 53 that interfaces with the bumper member 50 in order to limit translation of the spinal rods relative for each other. For instance, the bumper member 50 may limit motion of the cervical rod portion 41 in the bore 48 of the larger rod portion through interference with an end wall 55 of the cap portion 45. However, a gap 55 may be provided between the bumper 50 and the end of the thoracic/lumbar rod portion 42 in order to provide for some small amount of axial movement between the rod portions, depending on the movement and flexibility desired between the rod portions.

Figure 12:
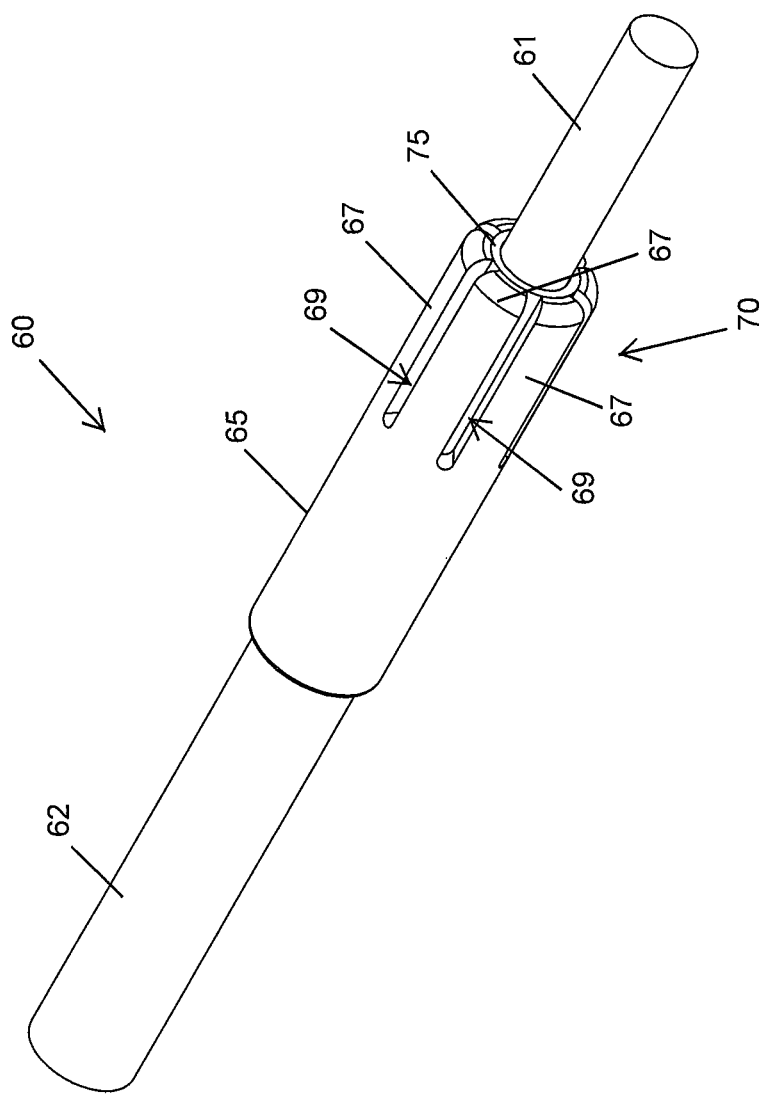
FIG. 12 is a perspective view of a spinal rod wherein a first rod portion is received within a cap portion at the end of a second rod portion that includes a number of projections to resiliently hold the first rod portion.
Figure 13:
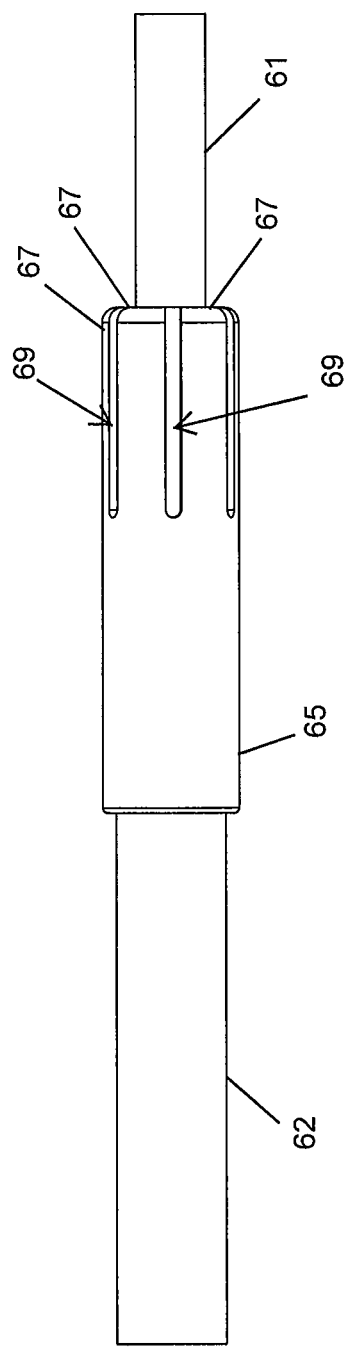
FIG. 13 is a side view of the spinal rod from FIG. 12.
Figure 14:
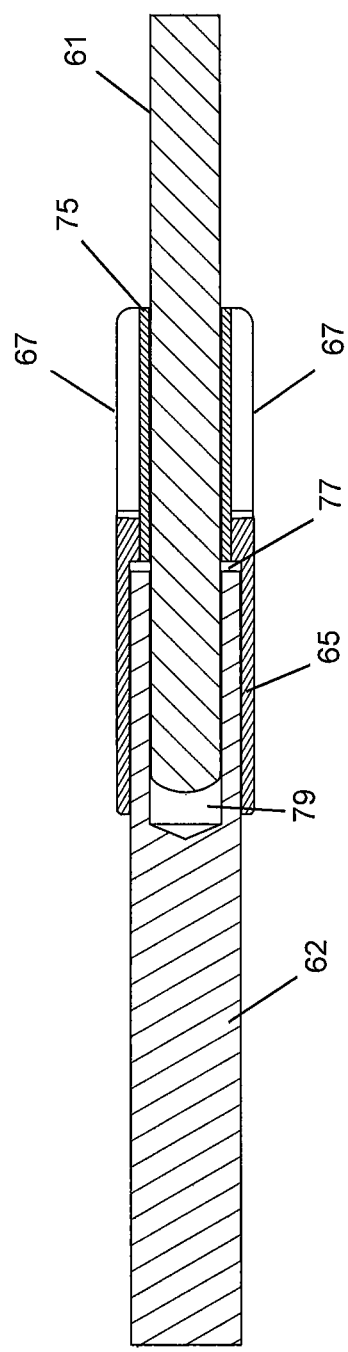
FIG. 14 is a cross-sectional view of the spinal rod from FIG. 12.

The spinal rod 60 in FIGS. 12-14 couples together two distinct rod portions 61 and 62 in a manner that allows some axial movement and flexing, alleviating some stress that may be imparted between the two rod portions. The transition region 70 is covered by a cap portion 65 which may be either a separate member or a unitary portion of one of the rod portions. The cap portion 65 includes a series of projections 67 and slits 69 that flexibly hold one of the rod portions (in this case, the smaller cervical rod portion 61). A polymer sleeve 75 is disposed between the cap portion 65 and the cervical rod 75 in order to grip the rod portion within the cap, and to provide additional flexibility to the transition region 70 between the two rod portions. The cross-sectional view of FIG. 14 shows that the cervical rod portion 61 is received within a bore 79 of the thoracic/lumbar rod portion 62, which is in turn surrounded by the cap portion 65. The polymer sleeve 75 surrounding a portion of the cervical rod portion 61 provides more flexibility than the fit between the wider rod portion 62 and the narrower rod portion 62, easing the transition in rod diameter. The spinal rod 60 may be configured to allow some axial movement between rod portions, such as by providing a gap 77 between the polymer sleeve 75 and the end of the thoracic/lumbar rod portion 62.

If desired, the polymer sleeve 75 may be composed of a metal or metal alloy rather than a polymeric material. Bumpers or grooves on the sleeve 75 or cervical rod portion 61, or other structures, may be provided in order to further limit axial movement between the rod portions. In addition, the cap portion 65 may be made up of the same material as one or both of the rod portions, or may be a different material. The rod portions and cap portion are preferably made up of stainless steel, titanium, cobalt-chromium alloys, nickel-titanium alloys, or polyetheretherketone (PEEK) or other similar polymers of the poly-aryl-ether-ketone family, or other suitable materials.

The preceding descriptions of implants have been presented only to illustrate and describe the present methods and systems, and are not intended to be exhaustive or to limit the present systems and methods to any precise form disclosed. Many modifications and variations are possible in light of the above teachings.

The foregoing embodiments were chosen and described in order to illustrate principles of the systems and methods as well as some practical applications. The preceding description enables others skilled in the art to utilize the methods and systems in various embodiments and with various modifications as are suited to the particular use contemplated.

What is claimed is:

1. A spinal stabilization system comprising:
   an elongate spinal rod having a longitudinal axis, a first axial region of a first diameter, and a second axial region of a second diameter larger than the first diameter of the first region;
   a third axial region of the spinal rod between the first and second axial regions thereof and including a plurality of annular grooves that progressively decrease in depth from the first axial region toward the second axial region;
   a plurality of annular collar portions of the spinal rod third region that each have the same outer diameter which, in turn, is the same as the larger second diameter of the spinal rod second region to provide the spinal rod third region with an effective diameter that is the same as the spinal rod second region with the collar portions axially spaced from adjacent collar portions by the annular grooves therebetween, the annual collar portions each having an outer surface at the outer diameter thereof with the outer surfaces of the annular collar portions each having a collar axial width extending along the longitudinal axis of the spinal rod sized so that the collar axial width is the same for each of the annular collar portions; and
   an endmost annular groove of the plurality of annular grooves that is adjacent to the first axial region and which has a groove diameter substantially the same as the first diameter with an endmost collar portion of the plurality of collar portions being between the endmost annular groove and the first axial region of the spinal rod.

2. The spinal stabilization system of claim 1 including a tapered portion that tapers down from the endmost collar portion to the smaller first diameter of the spinal rod first region.

3. The spinal stabilization system of claim 1 wherein the annular grooves each have an groove axial width along the spinal rod axis less than the collar axial width so that the adjacent collar portions are axially spaced from each other by the groove axial width that is less than the collar axial width of each of the collar portions.

* * * * *